United States Patent [19]

Ekholmer

[11] Patent Number: 4,620,564
[45] Date of Patent: Nov. 4, 1986

[54] DEVICE FOR REGULATING THE FLOW RATE IN A TUBE

[75] Inventor: Erik Ekholmer, Danderyd, Sweden

[73] Assignee: Mediplast AB, Solna, Sweden

[21] Appl. No.: 692,492

[22] Filed: Jan. 18, 1985

[30] Foreign Application Priority Data

Jan. 18, 1984 [SE] Sweden ................. 8400223

[51] Int. Cl.⁴ ............................ F16L 55/14
[52] U.S. Cl. ........................ 137/595; 251/4;
604/250; 137/601
[58] Field of Search ............ 251/4, 7, 8, 9;
137/595, 601, 212; 604/34, 250; 138/43

[56] References Cited

U.S. PATENT DOCUMENTS

| | | | |
|---|---|---|---|
| 2,516,029 | 7/1950 | Swindin | 251/9 |
| 2,569,850 | 10/1951 | Falconer | 251/4 X |
| 2,781,059 | 2/1957 | Frey | 138/46 |
| 3,062,239 | 11/1962 | O'Neill | 251/4 X |
| 3,322,147 | 5/1967 | Barrows | 137/595 |
| 3,720,235 | 3/1973 | Schrock | 138/46 X |
| 4,292,969 | 10/1981 | Raible et al. | 251/4 X |

OTHER PUBLICATIONS

SU-943-457, Ivan, Q66.
SU-706-634, Rozi, Q66.

Primary Examiner—Martin P. Schwadron
Assistant Examiner—Stephen M. Hepperle
Attorney, Agent, or Firm—Cushman, Darby & Cushman

[57] ABSTRACT

A device for regulating the flow rate in the tube, e.g. in infusion- and transfusion assemblies. The flow rate can be regulated by twisting a portion of the tube by means of a twisting device. The tube comprises at least along the portion of its length which is intended to be twisted a plurality of separate or communicating flow passages. Between said flow passages there are provided distance members arranged about or forming an inner core in the tube about which the tube is twisted and which reduces compression of the tube. When the tube is twisted the free space between said distance members is gradually reduced in the twisted cross-section of the tube and by that a reduction of the flow area is obtained.

10 Claims, 10 Drawing Figures

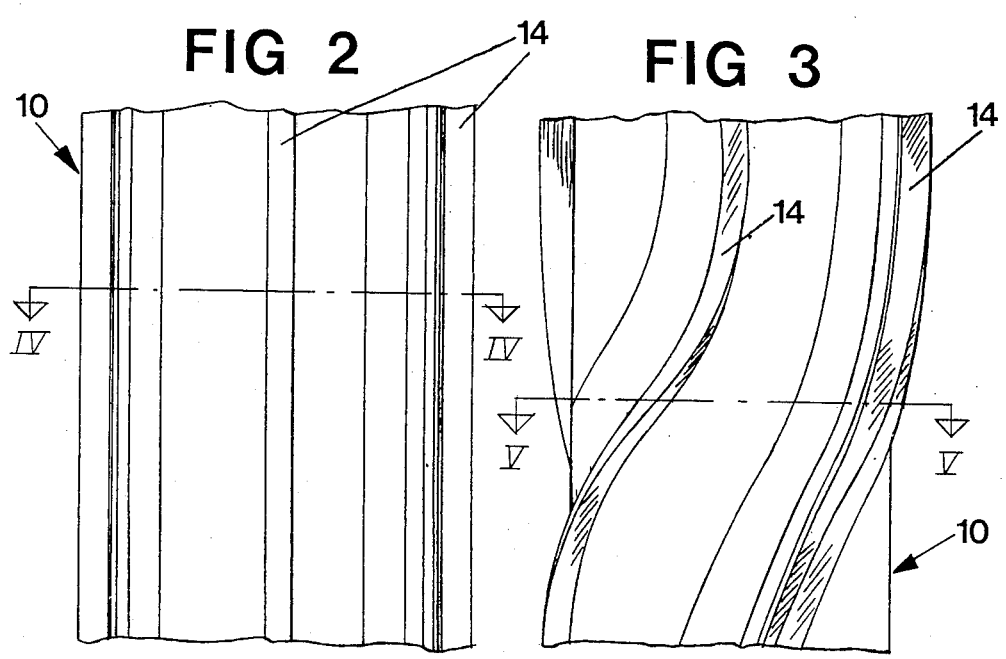
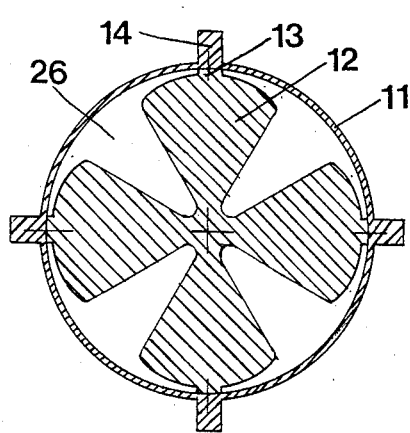
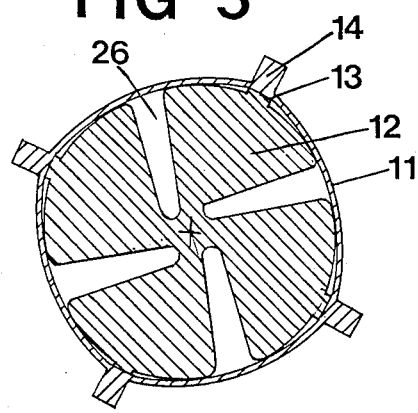

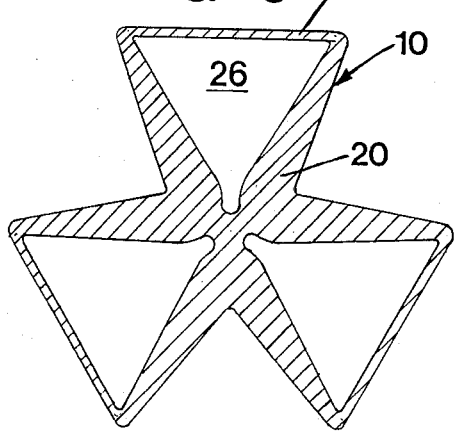
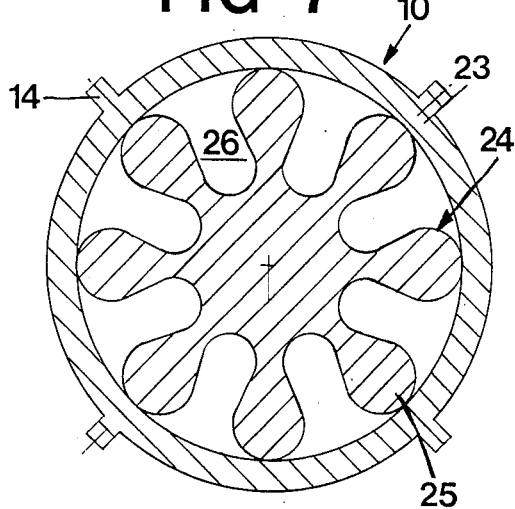
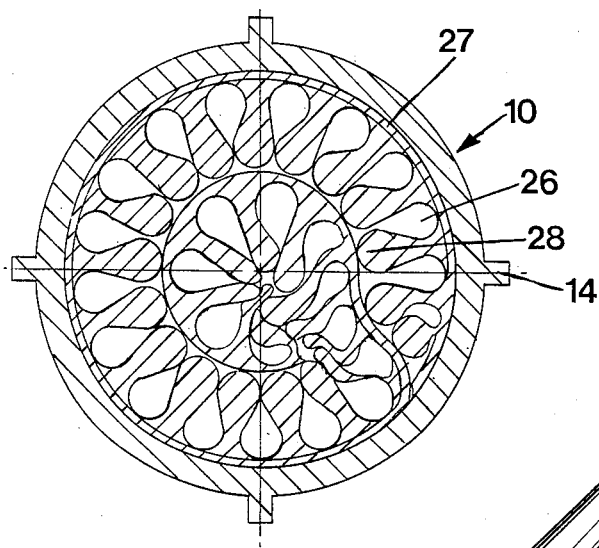
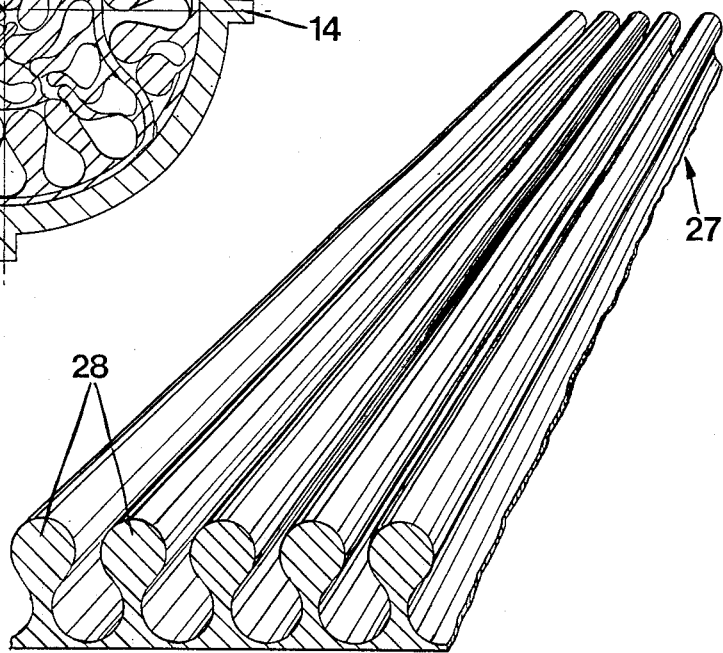

DEVICE FOR REGULATING THE FLOW RATE IN A TUBE

TECHNICAL FIELD

The present invention refers to a device for regulating the flow rate in a tube, for example in infusion- and transfusion assemblies, and which tube at least along a substantial part of its length comprises a plurality of separate or communicating flow passages, at which a device for regulating the flow rate in a tube, e.g. in infusion- and transfusion assemblies, and which tube at least along a part of its length comprises a plurality of separate or communicating flow passages, at which a twisting device is arranged on the tube for twisting a portion thereof in order to provide a gradual reduction of the flow area of the tube.

BACKGROUND OF THE INVENTION

The conventional way today to regulate the flow rate in tubes for infusion- and transfusion solutions is by means of clamping the tube in a so called roller clamp. It is however very difficult to provide an accurate adjustment of the flow area in the tube especially at low flow rates in this way. Besides the plastic material in the tube is exerted to high stresses at high degrees of compression and so called cold flow will easily occur. After this the ability of the tube material to revert its shape is detoriated. This is of course very unsatisfactory for infusion- and transfusion assemblies in medical treatment, where it is important that the drop rate can be set and adjusted with a high accuracy.

In SU-706-634 and SU-943-457 are shown valves for resilient cylinders for use in machine buildings and which valves are controlled by twisting the cylinders. On the inside of the cylinder longitudinal strips are arranged, which are intended to reduce the aerodynamic noise or which are filled with a thermo-sensitive material. These strips are however not designed to provide any substantial reduction of the compression of the cylinder when this is twisted. In order to provide a complete shut off of the flow a considerable twisting angle is required, which exerts the material in the cylinder to considerable stresses, and besides it is difficult to obtain an accurate adjustment of the flow area especially at low flow rate.

THE OBJECT AND MOST IMPORTANT FEATURES OF THE INVENTION

The object of the invention is to provide a device of the kind mentioned above, in which said drawbacks are avoided, at which the flow rate in the tube can be adjusted with a high accuracy. This has been provided by the fact that between said flow passages in the tube there are provided distance members arranged about or forming an inner core in the tube about which the tube is twisted and which reduces the compression of the tube.

DESCRIPTION OF THE DRAWINGS

The invention will now be described in detail with reference to some embodiments shown in the accompanying drawings.

FIG. 2 shows a portion of the tube on a larger scale.

FIG. 3 shows the same portion in a twisted position.

FIG. 4 is a section through the tube according to the line IV—IV in FIG. 2.

FIG. 5 is a section through the twisted portion of the tube according to the line V—V in FIG. 3.

FIGS. 6 and 7 are cross-sections through tubes according to other embodiments.

FIG. 8 shows in perspective an inset intended to be applied inside a tube.

FIG. 9 is a section through a tube provided with the inset according to FIG. 8.

DESCRIPTION OF THE EMBODIMENTS

Figure 1:
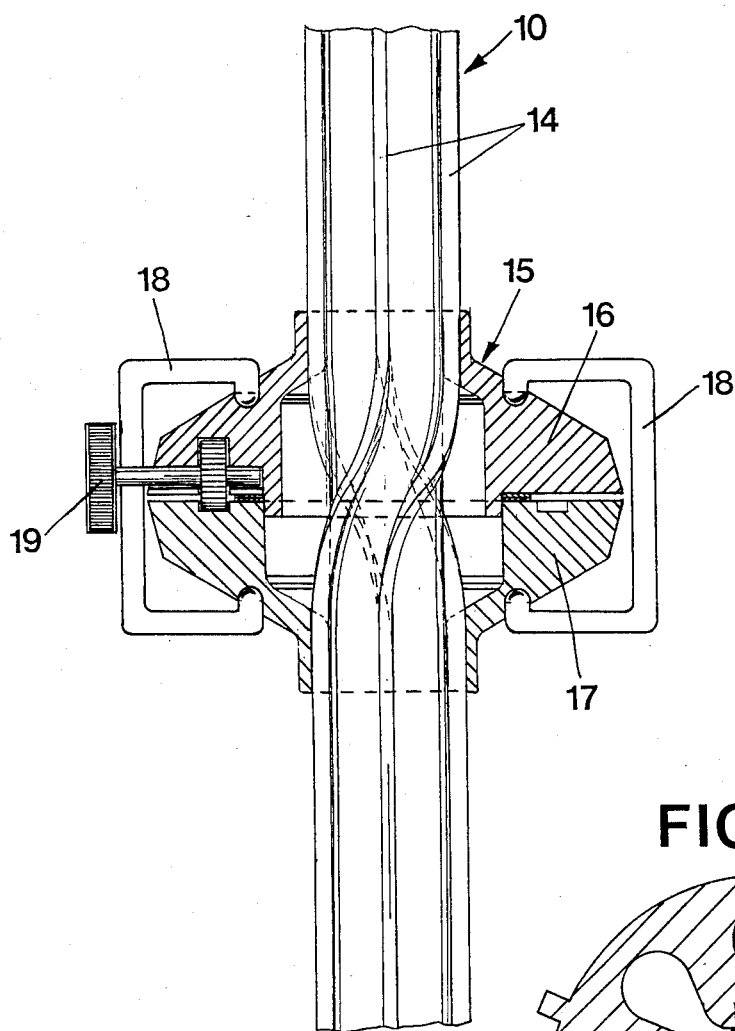
FIG. 1 shows a tube acording to the invention provided with a twisting device.

The tube 10 shown in FIGS. 1–5 consists of an outer tube 11 of a relatively soft plastic material, in which a number of radial arms 12 of a more rigid plastic material are arranged. These can, but not necessarily, be connected at the center of the tube. The tube is preferably manufactured by so called co-extrusion, and the arms 12 are connected with the outer tube 11 at the points 13. The outer tube 11, on its outside has longitudinal projections 14 arranged just opposite the connection points 13 between the outer tube 11 and the arms 12. These projections 14 make gripping members for twisting the tube. In the space between the arms 12 flow passages 26 are formed.

The twisting is provided by a twisting device 15, for example of the kind shown in FIG. 1. It comprises two members 16 and 17 rotatable with respect to each other, and which engage with the projections 14 of the tube. A pair of clamps keeps the members against each other. The lower member 17 can be rotated with respect to the upper member 16 by means of a handle 19, which meshes with teeth with a tooth segment in the lower member 17. The members are e.g. provided with friction surfaces for being frictionally locked to each other in any desired rotated position. In the twisting device curved inner grooves can further be arranged against which the projections 14 of the tube are bent and by that the twisting per length unit of the tube is controlled.

When the tube 10 is twisted the rigid arms 12 will be twisted about and around their respective center of gravity and radius of centre of gravity from the centerline of the tube. The substantially triangular or sector-shaped elements which make the arms 12 will by the twisting about the center line of the tube obtain an angle to the longitudinal axis of the tube, which angle is adjustable by the degree of twisting. Thus by the twisting the sector-shaped arm 12 is "tilted". The cross-sectional area of the tilted arm perpendiculary to the longitudinal axis of the tube is thus increased with an increased twisting (FIG. 5). The twisting angle for a completely closed tube is thus defined by the size of the arms with respect to the space between them. A considerably more accurate adjustment and regulation of the flow rate can be provided with this device as compared to a tube clamp which flattens the tube.

In FIG. 6 is shown a cross-section through a modified embodiment of a tube adapted for flow regulation by twisting. The tube 10 has a number of, in the shown example 3, substantially V-shaped profiles 20 having the apices directed towards each other. The apices can be connected to each other as shown but this is not necessary. In the later case it can be appropriate that the apices of the V-shaped profiles meet in the center of the tube. The V-shaped profiles 20 are connected to each other at their outer ends by means of connection walls 21 which preferably are thinner than the wall thickness of the profiles 20. When twisting the tube 10 the shanks of the profiles 20 will approach each other in the twisted cross-section with a gradual reduction of the free flow area as a result.

The cross-section of the tube shown in FIG. 7 is partly similar to the embodiment shown in FIGS. 2–5 and comprises an outer tube 23 and an inner core 24 with a plurality of radial longitudinal projections 25 which are connected to the outer tube 23. This tube is like the tube according to FIGS. 2–5 preferably manufactured by co-extrusion.

In the embodiment shown in FIG. 9 an inset 27 is arranged in a portion of the tube 10, which inset in a plane condition has the shape which can be seen in FIG. 8, i.e. it has a plurality of longitudinal projections 28. If the inset 27 is rolled together and is attached inside the tube 10 flow passages 26 will be formed between the projections 28. The flow rate in the tube is adjusted by twisting the tube just opposite the inset 27. The inset can of course be designed in many several ways, the purpose is however that it should form a plurality of communicating or separate flow channels inside the tube.

Figure 10:
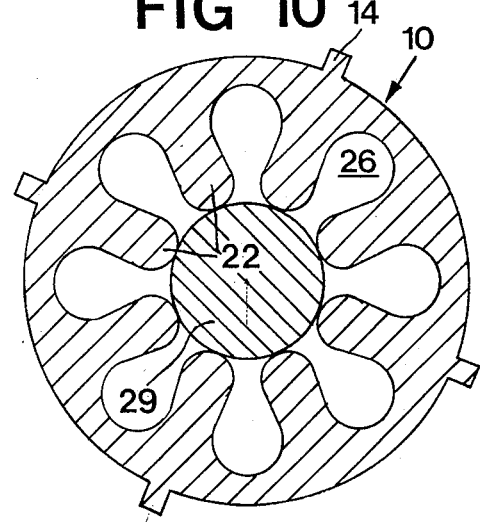
FIG. 10 shows a further embodiment of the invention.

In FIG. 10 is shown a further embodiment where the tube wall, on the inside is provided with a plurality of longitudional projections 22 arranged about an inner core 29 in the tube. The core 29 needs only to extend through that portion of the tube which is to be twisted and is preferably attached in the tube in a way so that it does not take part in the twisting movement.

The invention is of course not limited to the embodiments shown, but a plurality of modifications are possible within the scope of the claims.

I claim:

1. A device for regulating the flow rate in a tube, e.g. in infusion and transfusion assemblies, and which tube at least along a part of its length comprises a plurality of separate parallel flow passages, wherein each flow passage is formed by profile members and a section of a tube wall and a central impermeable core in the tube from which said profile members are attached and extend radially along the length of said central core outwards to the tube wall, a twisting device being arranged on the tube for twisting a portion thereof in order to provide a gradual reduction of the flow area of the tube the tube being twisted about said core, which reduces the compression of the tube.

2. A device as claimed in claim 1, wherein said profile members are arranged inside and firmly attached to an outer tube making the tube walls.

3. A device as claimed in claim 2, wherein said profile members are substantially triangular or sector-shaped having their base portion attached to the outer tube.

4. A device as claimed in claim 1, wherein the profile members are made of a less flexible material than the outer tube wall.

5. A device as claimed in claim 1, wherein said profile members are substantially V-shaped having their apices directed towards each other and which at their free ends are interconnected by means of connection walls, said connection walls being coextensive with the walls of the tube, so that a closed space is formed between said profiles.

6. A device as claimed in claim 5, wherein the profiles has a larger wall thickness than the connection walls.

7. A device as claimed in claim 1, wherein the inner core is provided with projections forming said profile members.

8. A device as claimed in claim 1, wherein said twisting device comprises a pair of members attached opposite each other and which are unrotatably connected to the tube, rotating means being provided for rotating the members relative to each other and said members being self-locking or provided with locking means for being locked to each other in any desired rotated position.

9. A tube assembly for controlling the flow rate of liquid therethrough, said tube assembly comprising:
  a central core disposed within said tube assembly along a longitudinal axis;
  a plurality of profile members extending radially from said central core to the wall of said tube assembly, said profile members being substantially V-shaped having their apices directed towards each other and which at their free ends are interconnected by means of connection walls, so that a closed spaced is formed between said profile members; and
  a twisting device arranged on the exterior of said tube assembly for twisting a portion of said tube assembly around said central core.

10. A device as claimed in claim 9, wherein said profile members have a larger thickness than said connection walls.

* * * * *